United States Patent [19]

Siri

[11] Patent Number: Plant 5,305

[45] Date of Patent: Oct. 23, 1984

[54] MINIATURE CARNATION

[75] Inventor: Angelo J. Siri, San Francisco, Calif.

[73] Assignee: Siri Brothers Nursery, Inc., East Palo Alto, Calif.

[21] Appl. No.: 397,118

[22] Filed: Jul. 12, 1982

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Limbach, Limbach & Sutton

[57] ABSTRACT

A miniature carnation having blossoms of pale lilac with darker lilac stripes and blotches.

4 Drawing Figures

BACKGROUND OF THE NEW PLANT

This invention comprises a new and distinct miniature carnation variety that has its own set of characteristics that set it apart from all other varieties of miniature carnations. The newly discovered variety, called "Variegated Lilac," originated as a sport of Petite Purple, a patented variety, U.S. Plant Pat. No. 3,767.

The botanical classification of the new variety is *Dianthus caryophyllus Longicaulis.* The commercial classification is Miniature Carnation. The plant takes the form of a bush.

Asexual propagation of the newly discovered miniature carnation variety has been made at Siri Brothers Nursery, Inc. at East Palo Alto, Calif. by taking cuttings. The cuttings so taken and grown, have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

Figure 1:
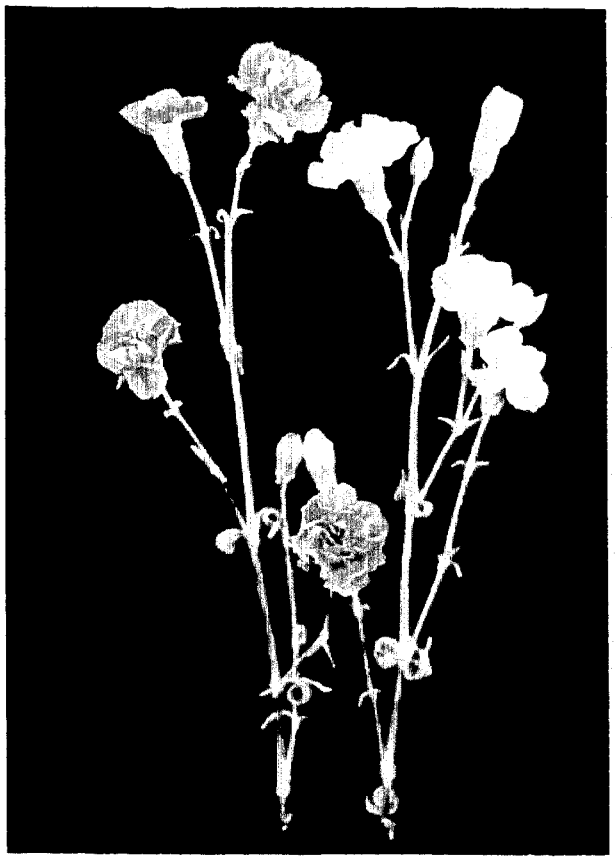
FIG. 1. PRIOR ART
FIG. 1 shows sprays and stems of the new variety Variegated Lilac on the right and the prior Petite Purple on the left.
Figure 2:
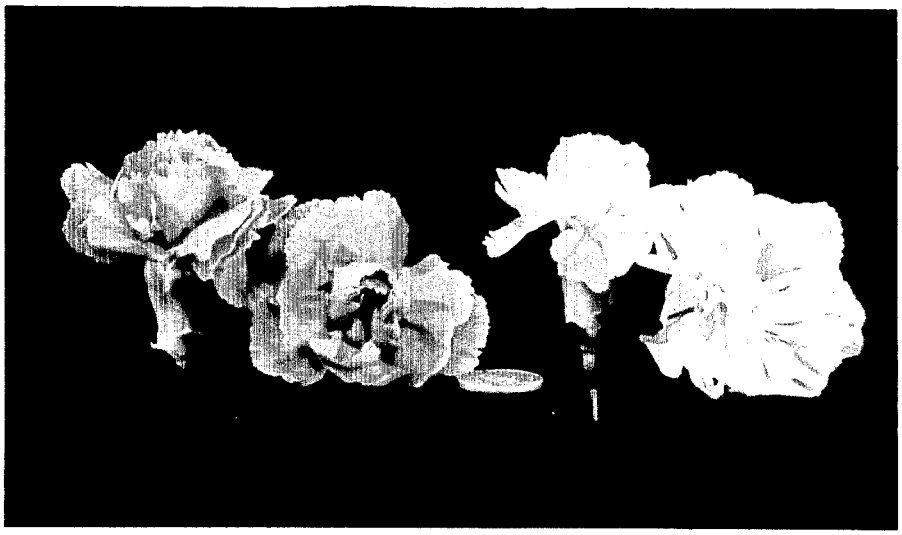
FIG. 2 shows the blooms of the new variety variegated Lilac on the right and prior Petite Purple on the left.
Figure 4:
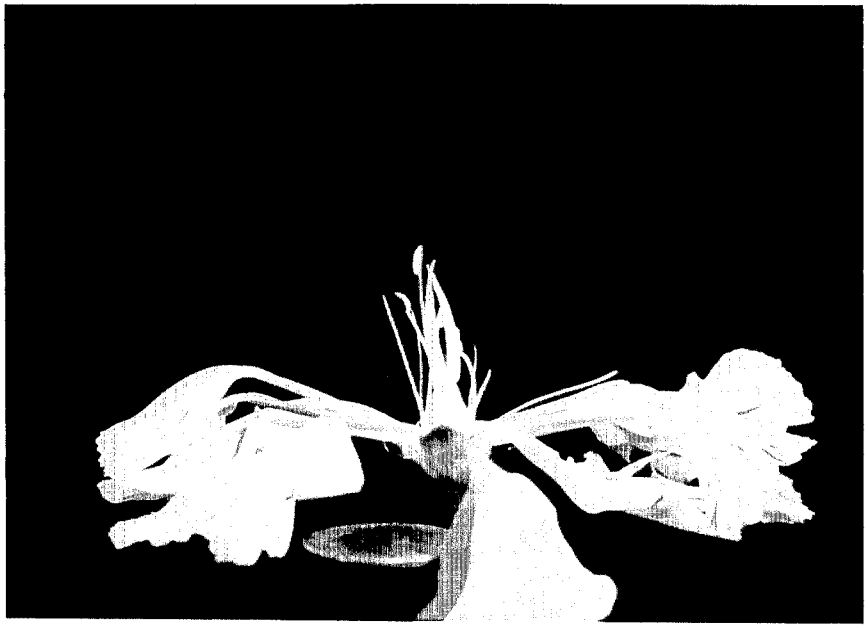
FIG. 4 shows the interior of the new variety Variegated Lilac. The photographs are somewhat overexposed.
Figure 3:
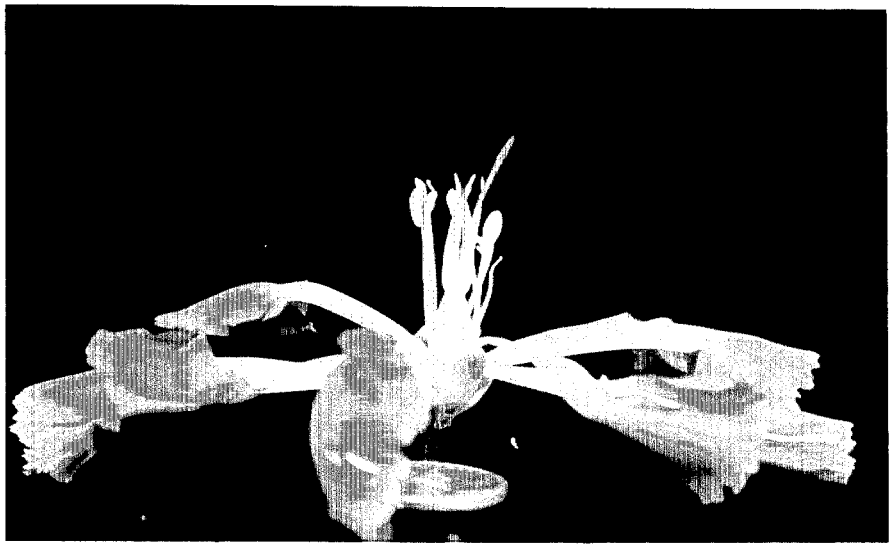
FIG. 3. PRIOR ART
FIG. 3 shows the interior of the prior Petite Purple.

The following detailed description of the new variety is based on my detailed observations of the new cultivar which were made at Siri Brothers Nursery Inc. at 940 O'Connor Street, East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore Md. and "R.H.S." for Royal Horticultural Color Chart, The Royal Horticultural Society, London, England.

GROWTH HABITS

Height: Short to medium.

Foliage: Average.

Speed of growth: Fast.

Root system: Average.

FOLIAGE

Leaf size:

*Length varies.*—Longer at the bottom of the stem and shorter at the top of the stem. Average length at the middle of the stem 4 inches.

*Width varies.*—Wider at the bottom of the stem and thinner at the top of the stem. The average width at the middle of the stem is $\frac{3}{8}$ of an inch.

*Features.*—N/A.

Leaf shape: Very little curl with a long acuminating tip.

Leaf texture: Smooth and leathery.

Leaf color:

*Upperside.*—R.H.S. Green Group 139A with a whitish color over the green.

*Underside.*—Same as upperside.

Leaf ribs: One rib down the center fom the base to the tip of the leaf.

Leaf habit: Very little curl.

Leaf density: Average.

STEM

Stem strength: Average.

Stem color: R.H.S. Green Group 139A with a whitish color over the green.

Nodes: Average.

*Space between nodes.*—$3\frac{1}{2}$ Inches is the average at mid-stem.

Stem branching: Very good, wide gaps between the branches. It is not clubby.

BUDS

Bud shape: Oval.

Bud color: Top half of bud is LCC H-21 L-13, the bottom half blends into LCC H-22 L-9.

Average number of flowering buds per stem: 4 to 5.

Uniformity of bud opening: Very uniform.

Bud splitting: Very seldom.

Number of sepals per calyx: 75% of the buds have 5 sepals, 25% of the buds have 6 sepals.

FLOWER

Description of the color of the bloom: Both blossoms shown in the drawings are somewhat overexposed. The bloom is a lavender or lilac color which can range from LCC H-44 L-1 to LCC H-44 L-3 with purple colored blotches and stripes (LCC H-43 L-14 top side of petal and LCC H-43 L-13 underside of petal) of varying size that run from the base of the bloom to the outer edge. However, there are some purple blotches and stripes that run in the petal but do not touch the base or the outer edge, or in some cases they may touch either the base or the outer edge but not both. Where the purple does not touch the outer edge there is a very light pink, that appears white, fringe that is approximately 1/16 of an inch wide at the outer edge of the petal. The color of the fringe is LCC H-44 L-1 both topside and underside. On occasion there are even some petals that are completely lilac or completely purple. There is no exact set pattern to the purple blotches and stripes although there is a consistent one.

Diameter of average bloom: 2¼ Inches.

Bloom shape: Generally round with a high center and a flat outer petal.

Keeping quality: Average.

Fragrance: Slight.

PETALAGE

Petal texture: Soft and velvety.

Petal edge: Slight serration.

Petal color: As stated above.

Color stability: Very good, only a slight reversion to petite purple.

Petal size:

*Average length.*—1 13/16 Inches.

*Average width at widest point.*—1 Inch.

Calyx color: The top half is LCC H-21 L-13, the bottom half is LCC H-22 L-9. The tip of the leaves on the side of the calyx is LCC H-22 L-15.

REPRODUCTIVE ORGANS

Stamen: Both with and without anthers. Approximately 90% of stamen have anthers and 10% do not.

Average length of stamen: 1⅛ Inches.

Color of anthers: LCC H-48 L-4.

Color of filament: LCC H-21 L-1.

Pistils:

*Shape.*—88% Have 2 styles, 6% have 1 style, and 6% have 3 styles.

*Number.*—One.

*Length from tip to ovary.*—Approximately ⅞ of an inch.

Stigma:

*Shape.*—Round, located at the very tip of the style.

*Color.*—White.

Style:

*Color.*—LCC H-25 L-1 with the purple color LCC H-43 L-14 toward the tip and at other parts of the style.

Ovary:

*Shape.*—Ovid.

*Color.*—Top half LCC H-22 L-4, bottom half LCC H-23 L-2.

*Length.*—⅜ Of an inch.

*Width.*—3/16 Of an inch.

DISTINGUISHING CHARACTERISTICS BETWEEN THE NEW VARIETY AND PARENT

The primary distinguishing characteristic of the two varieties is the color itself. Petite purple is a solid purple while Variegated Lilac is a lilac color with purple blotches and stripes. Petite purple has much more of the purple color LCC H-43 L-14 on its styles than does Variegated Lilac. The anthers of Petite Purple are the color LCC H-48 L-8 while the color of the anthers of Variegated Lilac are LCC H-48 L-4.

SIMILAR CHARACTERISTICS OF THE NEW VARIETY AND PARENT

All of the characteristics of both varieties are similar except for the distinguishing characteristics referred to above.

I claim:

1. A new and distinct variety of miniature carnation plant, substantially as herein shown and described.

* * * * *

PRIOR ART